United States Patent

George et al.

[11] Patent Number: 4,468,219
[45] Date of Patent: Aug. 28, 1984

[54] PUMP FLOW RATE COMPENSATION SYSTEM

[75] Inventors: Dennis R. George, Hamilton Square; Michael J. Steinmetz, Jackson; Robert A. Weber, Plainsboro, all of N.J.

[73] Assignee: International Business Machines Corporation, Armonk, N.Y.

[21] Appl. No.: 563,718

[22] Filed: Dec. 20, 1983

[51] Int. Cl.³ ............................................. A61M 1/03
[52] U.S. Cl. ............................ 604/66; 128/DIG. 12; 604/67
[58] Field of Search .......................... 604/50, 66, 67; 128/DIG. 12, DIG. 13

[56] References Cited

U.S. PATENT DOCUMENTS

| | | | |
|---|---|---|---|
| 3,882,861 | 5/1975 | Kettering et al. | 128/214 |
| 3,946,731 | 3/1976 | Lichtenstein | 128/214 |
| 4,055,175 | 10/1977 | Clemens et al. | 128/213 |
| 4,077,405 | 3/1978 | Haerten et al. | 128/DIG. 12 X |
| 4,080,966 | 3/1978 | McNally | 128/214 |
| 4,245,634 | 1/1981 | Albisser et al. | 604/66 |
| 4,280,494 | 7/1981 | Cosgrove et al. | 604/66 X |
| 4,392,849 | 7/1983 | Petre et al. | 604/66 |

Primary Examiner—Edward M. Coven
Attorney, Agent, or Firm—Thomas J. Kilgannon

[57] ABSTRACT

This invention relates generally to systems for handling biological fluids such as blood and more particularly relates to apparatus for maintaining a constant flow rate of fluid by a peristaltic pump when the pressure at the input of such a pump goes negative or positive. More specifically, the invention uses a microprocessor which provides an output signal representative of the incremental change in pump speed required when the pump input experiences a negative or positive pressure regime.

The microprocessor output is based on a sensed input pump pressure, $P_o$, a pressure, $P_i$, which is the pressure at which extensions of the linearly decreasing portions of the pump characteristic curves intersect the pressure axis on a plot of Pressure vs Flow Rate for a given pump and a desired flow rate, $Q_o$. The resulting output is applied to a stepper motor via a programmable timer and driver amplifier. The motor mechanically linked to the pump drives the pump at a speed which maintains the flow rate constant.

9 Claims, 3 Drawing Figures

PUMP FLOW RATE COMPENSATION SYSTEM

DESCRIPTION

Technical Field

This invention relates generally to systems for handling biological fluids such as blood and more particularly relates to apparatus for maintaining a constant flow rate of fluid by a peristaltic pump when the pressure at the input of such a pump goes negative or positive. More specifically, the invention uses a microprocessor which provides an output signal representative of the incremental change in pump speed required when the pump input experiences a negative pressure regime.

The microprocessor output is based on a sensed input pump pressure, $P_o$, a pressure, $P_i$, which is the pressure at which extensions of the linearly decreasing portions of the pump characteristic curves intersect the pressure axis on a plot of Pressure vs Flow Rate for a given pump and a desired flow rate, $Q_o$. The resulting output is applied to a stepper motor via a programmable timer and driver amplifier. The motor mechanically linked to the pump drives the pump at a speed which maintains the flow rate constant.

BACKGROUND OF THE INVENTION

In the processing of biological fluids such as blood where a patient is connected to the blood processing apparatus as part of a closed system, one of the major objectives is to maintain a constant flow rate of blood to the processing apparatus under conditions which include pressure variation from positive to negative at the input of a peristaltic pump. The pressure variations can arise from a number of sources including blood pressure drops in the patient and may vary quite widely in the course of a blood processing run.

The variations in flow rate due to pressure variations can be minimized by either using stiffer tubing or by restricting the allowable input pressure. The former approach, however, increases the torque requirements on the pump which, in turn, requires a larger motor while the latter approach may not be possible because of system requirements.

U.S. Pat. No. 3,882,861 filed Sept. 24, 1973 and issued May 13, 1975 shows an auxiliary control for a blood pump which acts on an existing blood pump controller to continuously vary the pump rate in direct correspondence with changes in flow of a patient's blood reflected as variations in negative pressure in a blood line. In this patent, the the negative pressure is sensed upstream from the pump such that when blood flow decreases (greater negative pressure is sensed), the speed of the pump is decreased and, when blood flow increases (lesser negative pressure is sensed), the speed of the pump is increased. Thus, pump starvation caused by vacuum-induced collapse of blood lines and blood vessels is avoided because the pump will operate only at the maximum rate accommodated by the available blood supply. The present invention differs from the patent in that it seeks to maintain a constant flow rate to the input of a pump the flow rate of which changes in accordance with the pump characteristic when the input pressure to the pump enters a negative pressure regime. The patent doesn't appear to be constrained in any way by the pump characteristic and reduces speed when blood flow decreases and increases speed when blood flow increases while, in the present invention, pressure is sensed at the input of the pump and the pump speed is increased in the face of decreasing blood flow. The patent seeks to maintain a constant negative pressure whereas the present invention seeks to maintain a constant flow rate regardless of the variation in negative pressure.

U.S. Pat. No. 4,055,175 filed May 7, 1976 and issued Oct. 25, 1977 shows a sensor, computer and pump system whereby insulin is infused by a pump into a patient under control of a computer which is programmed to provide desired output signals based on sensed blood glucose concentration. In the patent, neither pressure nor flow rate in the pump is continuously controlled. Only the glucose infusion rate is controlled with no consideration being given to the pump characteristic, if any.

U.S. Pat. No. 4,080,966 filed Aug. 12, 1976 and issued March 28, 1978 shows supplying a hypertensive control agent in response to increased blood pressure by a controller. The output of the latter controls a pump. There is no teaching of sensing pump input pressure nor is any means shown for maintaining a constant flow rate.

U.S. Pat. No. 3,946,731 filed July 31, 1974 and issued March 30, 1976 shows a blood treatment system where pressure is sensed downstream of the pump and a signal applied to a controller which controls the rate of pumping in the event the sensed pressure moves towards one or the other of preselected limits. In this patent, the intent appears to be to maintain a constant pressure at the pump input whereas, in the present invention, the intent is to maintain the flow rate constant regardless of pressure variation.

It is, therefore, an object of the present invention to provide a microprocessor controlled system in which flow rate of blood or other biological fluid through a peristaltic pump is maintained constant regardless of variations in negative pressure at the pump input.

Another object is to provide a system for pumping blood in which the pressure vs flow rate characteristic of a pump in the negative pressure regime is compensated for by increasing pump speed in accordance with the relationship $$S = \frac{P_i}{P_i - P_o} S_o.$$

Still another object is to provide a system for pumping blood which permits control of flow rate in real time by means of a microprocessor which is responsive to sensed input pump pressure, a pressure determined from the pump characteristic and a desired flow rate.

BRIEF SUMMARY OF THE INVENTION

The present invention relates to apparatus for maintaining the flow rate of a peristaltic pump constant when the pump experiences input pressure variations in the negative pressure portion of its pump characteristic. Under such circumstances, the reduction in flow rate can be broadly compensated for by manually increasing the pump speed but this tactic is, for the most part, time consuming and ineffective to do more than provide a ballpark adjustment. Other expedients such as the use of stiffer tubing and larger motors are expensive and represent fixed conditions which are not subject to fine control. The present apparatus overcomes these objections by sensing the input pressure to the pump by means of a noninvasive pressure sensor. The analog output of the sensor is converted by an analog-to-digital converter (ADC) and applied as an input to an appropriately programmed commercially available microprocessor. Other inputs to the microprocessor are the desired flow rate, $Q_o$, a pump constant K and a constant, $P_i$, obtained from the pump characteristic (Pressure vs Flow Rate) plot.

For pressures equal to or greater than zero, the flow rate is essentially constant and, therefore, the pump speed required to produce a given flow rate is constant. However, for pressure less than zero, the flow rate drops off with pressure if the pump speed is held constant. The drop is linear up to a point and then it rapidly falls to zero. If the linear portion of the curves for different flow rates are extrapolated to the pressure axis, they tend to intersect at the same point, $P_i$. The latter is constant for a given pumping system. For P=0, then, the pump speed is given by $S_o = KQ_o$ where:

$Q_o$ = desired flow rate (ml/min)
K = pump constant
$S_o$ = pump speed (RPM).

However, for P<o, the speed must be increased to maintain constant flow. The correction factor is determined from the pump characteristic plot as follows:

Using similar triangles $$\frac{Q}{P_i} = \frac{Q_o}{P_i - P_o} \text{ where:}$$

$P_o$ = pressure determined by a sensor
Q = equivalent flow rate at zero pressure at which $Q_o$ is obtained when pressure is $P_o$
Q = KS and $Q_o = KS_o$, so by substitution $$S = \frac{P_i}{P_i - P_o} S_o$$

where the term $P_i/(P_i - P_o)$ is the correction factor by which the speed $S_o$ must be changed to achieve the desired flow rate, $Q_o$, at $P_o$.

With a desired flow rate, $Q_o$, the pump constant K and $P_i$, entered into the microprocessor, the processor continuously samples the output of the ADC and computes the correction factor. The latter is used to obtain a signal which drives a stepper motor to the new required speed.

These and other objects, features and advantages will be more apparent from the following more particular description of the preferred embodiments.

BRIEF DESCRIPTION OF THE DRAWINGS

Referring now to FIG. 1, there is shown a plot of Pressure (P) vs Flow Rate (Q) for a peristaltic pump of the kind used in the practice of the present invention. Let it suffice to say, at this juncture, that the pump utilized does not depart to any great extent from those utilized by practitioners in the art of blood processing.

Figure 1:
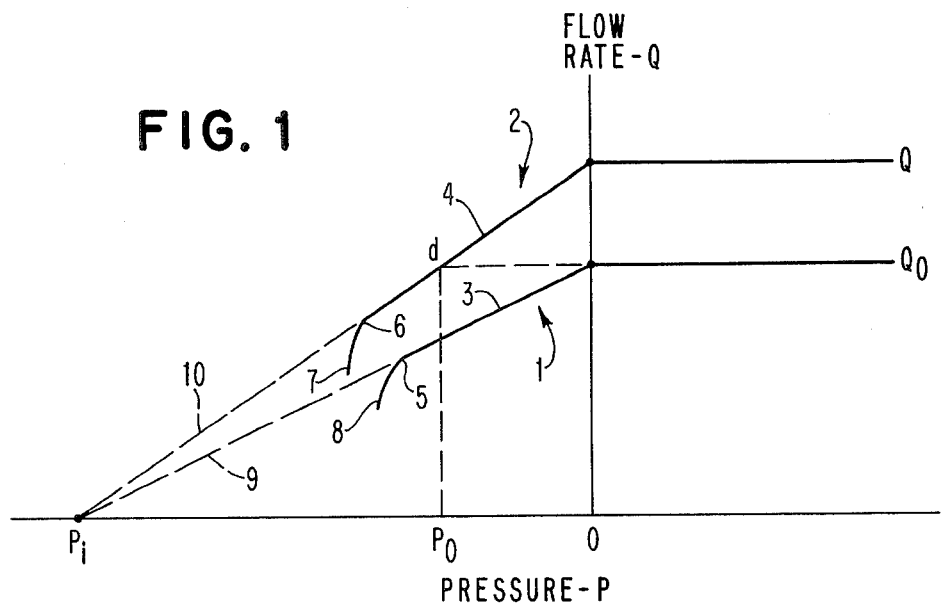
FIG. 1 is a plot of input Pressure (P) vs Flow Rate (Q) for a peristaltic pump. The plot is otherwise known as the pump characteristic and includes a pair of characteristic curves which show the variation in pressure and flow rate for two speeds.

The plot of FIG. 1 is otherwise known as the pump characteristic for a given type of pump and usually includes a plurality or family of characteristic curves which show the variation in Flow Rate (Q) with Pressure (P) for different pump speeds. Only two of these characteristic curves have been shown in FIG. 1 to clearly show the concept involved in utilizing the present invention.

In FIG. 1, characteristic curves 1, 2, for pressures of zero and greater than zero at the input of a peristaltic pump and for two different speeds, show constant flow rates. In general, for positive pressures Q = KS; where
Q = Flow Rate milliliters/minutes
S = Pump speed in RPM, and
K = Pump constant in milliliters/revolution.

For pressure equal to or greater than zero, the flow rate is essentially constant and, therefore, the pump speed required to produce a given flow rate is constant. However, for pressures less than zero, if the pump speed is held constant, the flow rate drops off linearly with pressure as shown at portions 3,4 of curves 1,2, respectively. The variation is linear up to points 5,6 on curves 1,2, respectively, at which points, the flow rates rapidly fall toward zero as shown by dashed line portions 7,8 on curves 1,2, respectively. The present inventors have determined that if one extrapolates linear portions 3,4 of curves 1,2, respectively, to the pressure axis as shown by dashed lines 9,10, respectively, in FIG. 1, dashed lines 9,10 tend to intersect at the same point, $P_i$. For any given pump system which includes factors such as pump head, tubing, etc., point $P_i$ is fixed.

To the extent that flow rate is directly proportional to pump speed, it follows that, when the flow rate drops off that to maintain the same flow rate, the pump speed must be increased. For pressures of zero and greater than zero, this speed determination is relatively simple in view of the direct relation between flow rate and speed. However, for pressures less than zero, while the relationship between speed and flow rate is still directly proportional, until now, there was no simple way of determining the speed at which a pump must be driven in order to achieve a desired flow rate. Having determined that $P_i$ is substantially fixed for a given pumping system, applicants appreciated by using the relationships involved in similar triangles that a determination could be made, in real time, which provides a desired pump speed when the pump input pressure drops below zero.

Referring again to FIG. 1 and assuming that a pump system is operating in a positive pressure regime on characteristic curve 1 and that a desired flow rate, $Q_o$, is being provided, the speed, $S_o$, is obtained in accordance with the relationship, $S_o = KQ_o$.

If during operation the input pressure drops below zero and the pump speed remains constant, the flow rate drops off and, if the same flow rate is to be maintained, the speed must be increased by some amount. This amount can be determined by first appreciating that, if it is desired to maintain the same flow rate, this can be done by using another characteristic curve which provides higher flow rates and therefore requires higher pump speeds. The proper characteristic curve is selected by identifying a point on it which is determined by the values of $P_o$ and $Q_o$. The curve selected now represents the flow rate, Q, which will provide the desired flow rate, $Q_o$, when the pressure drops to $P_o$. From the value Q, pump speed, S, can be calculated. Thus, in FIG. 1, if the input pressure drops to $P_o$, the point of intersection between the dashed lines $P_o$—d and $Q_o$—d determines a point on a new characteristic curve. If this point is connected with point $P_i$ and extended to the P=O axis, it will intersect that axis at a flow rate Q which is proportional to a new speed, S. The latter speed is then the speed which will provide the desired flow rate, $Q_o$, on the new characteristic curve 2 when the pressure on the pump input drops to a pressure, $P_o$.

Using similar triangles the value of Q can be mathematically determined as follows from FIG. 1:

$$\frac{Q}{P_i} = \frac{Q_o}{P_i - P_o} \text{ where}$$

$P_i$ is a fixed and known value for a given pump system, $P_o$ is the pressure less than zero to which the input pressure drops, $Q_o$ is the desired flow rate to be maintained regardless of pressure, and Q is the new flow rate at zero pressure which, at the pressure $P_o$, provides the desired flow rate.

Knowing that $S_o = KQ_o$ where $S_o$ is the speed which provides the flow rate $Q_o$ on characteristic curve 1 and that $S = KQ$ where S is the new speed which provides flow rate Q on characteristic curve 2, S can be determined directly by substitution providing the result:

$$S = \frac{P_i}{P_i - P_o} S_o.$$

The above relationship can easily be provided in real time utilizing a microprocessor which has as its inputs the sensed pressure at the input $P_o$, the fixed value for a given pump system, $P_i$ and the speed, $S_o$, as determined from the desired flow rate. By multiplying the speed $S_o$ by the factor $P_i/(P_i-P_o)$, the new speed S is determined. In this way, a constant flow rate can be maintained under conditions of changing negative pressure.

Figure 2:
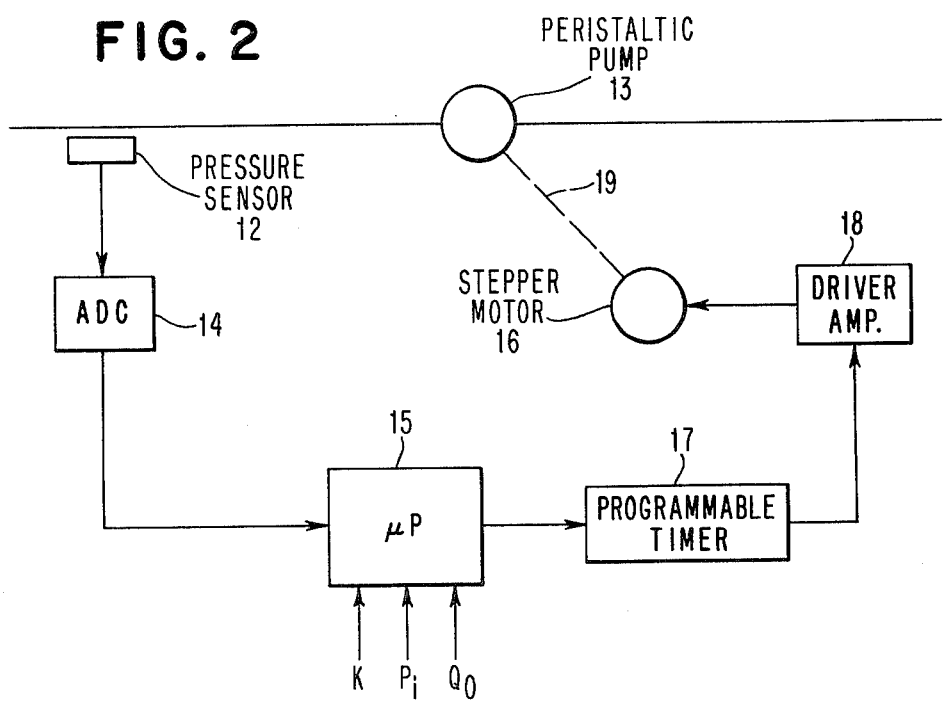
FIG. 2 is a partially schematic block diagram of a pumping system which, in accordance with the teaching of the present invention, provides a constant flow rate under conditions of changing negative pressure.

Referring now to FIG. 2, there is shown a partially schematic block diagram of a pumping system which, in accordance with the teaching of the present invention, provides a constant flow rate under conditions of changing negative pressure. The system includes a microprocessor which provides at its output a correction factor $P_i/(P_i-P_o)$ which adjusts the speed of a stepping motor from its previous speed to a new speed.

In FIG. 2, a partially schematic block diagram of a pump system 11 is shown which includes a pressure sensor 12 for determining the pressure at the input port of a peristaltic pump 13. Pressure sensor 12 provides an analog output which is provided to the input of an Analog-to-Digital Converter (ADC) 14. The output of ADC 14 is applied as one input to a microprocessor (uP) 15. The value of $P_i$ which is the pressure at which the linearly decreasing extensions of the pump characteristic curves intersect the pressure axis and the value of $Q_o$ which is the desired constant flow rate at positive pressures are stored in microprocessor 15. The latter provides at its output a digital signal which is representative of the amount by which the speed $S_o$ must be changed to obtain the pump speed at which a stepper motor 16 must be driven to maintain a constant flow rate $Q_o$. In addition, the pump constant, K, which is a fixed value for a given pump, is applied as an input to microprocessor 15. The resulting output is applied to a programmable timer 17 the output of which is a square wave. The frequency of the square wave determines the speed of stepper motor 16. The square wave output is applied to motor 16 via a driver amplifier 18. Motor 16, in turn, drives peristaltic pump 13 by means of a mechanical linkage indicated by dashed line 19 in FIG. 2.

While operation of the present system has been discussed above in connection with pressure variations in the negative pressure regime, it should be appreciated that the same approach can be utilized with pressure variations the positive regime.

Figure 3:
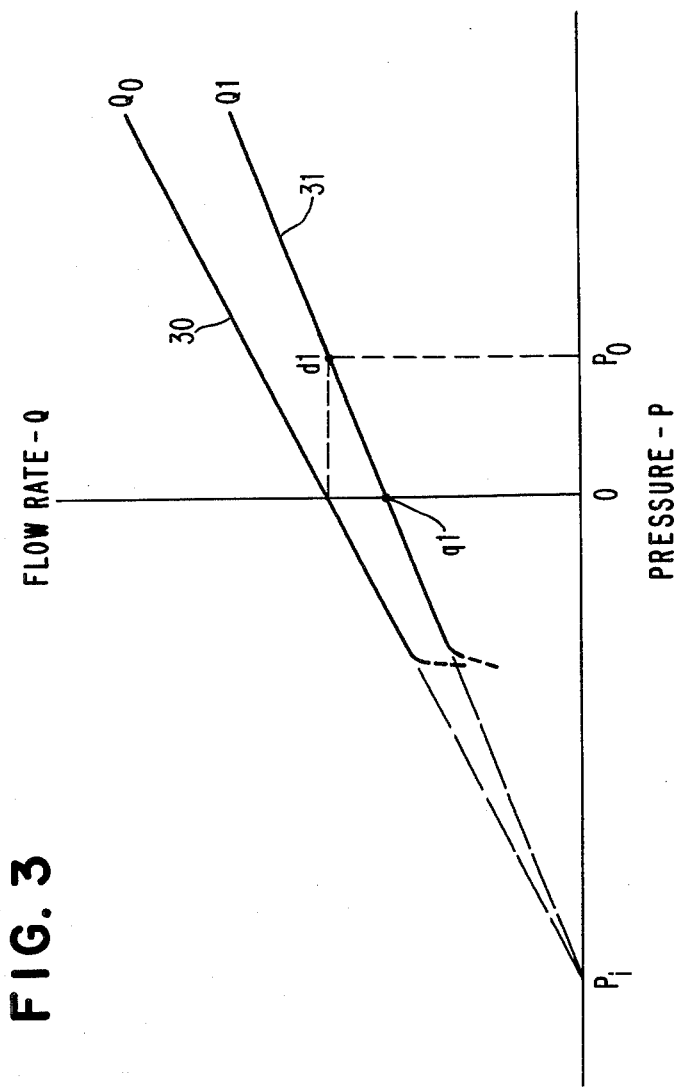
FIG. 3 is a plot of input Pressure (P) vs Flow Rate (Q) for a peristaltic pump similar to that shown in FIG. 1 except that the Flow Rate varies linearly with pressure for pressures greater than zero.

Referring now to FIG. 3, there is shown a pair of characteristic curves 30,31 otherwise labeled in FIG. 3 by the references $Q_o$, Q1, respectively. Both of these curves show linear variations in flow rate with pressure in the positive pressure regime. Thus, if it is desired to maintain a constant flow rate regardless of the pressure, it follows that the pump speed must be reduced to some lower speed. The new, lower speed can be determined from FIG. 3 using similar triangle principles by extending $Q_o$ to the right until it intersects the positive pump input pressure $P_o$ at point d1. The curve selected is on characteristic curve 31 which now represents the flow rate Q1, which will provide the desired flow rate, $Q_o$ when the pressure increases to $P_o$. In order to maintain the desired constant flow rate $Q_o$ at a pressure $P_o$, the flow rate and therefore the speed at zero pressure must be determined. This is point q1 in FIG. 3 where characteristic curve 31 intersects the zero pressure axis. The value of flow rate and, therefore, speed can be determined from the following relationship using the triangles $P_iP_o$ d1 and $P_i$ O q1:

$$\frac{Q_o}{Q1} = \frac{P_i + P_o}{P_i}$$

$$Q1 = S1 = \frac{P_i}{P_i + P_o} S_o.$$

The term $P_i/(P_i+P_o)$ is the factor by which the pump speed $S_o$, at zero pressure must be reduced to provide the constant flow rate $Q_o$ at a pump input pressure $P_o$. The new speed S1 is $S_o$ multiplied by the term $P_i/(P_i+P_o)$. The overall system operation in the positive pressure regime is the same as that described hereinabove in connection with the negative pressure regime operation.

In practice, the system of FIG. 2 is utilized in conjunction with blood processing apparatus such as the IBM 2997 Blood Processor which incorporates a centrifuge which separates blood into its constituents. The system is closed in that whole blood is taken from a patient, processed in the centrifuge and certain of the constituents are returned directly to the patient. In addition to the above mentioned IBM 2997 Blood Processor, all the elements discussed in connection with FIG. 2 are available from commercial sources. Thus, pressure sensor 12 is a noninvasive pressure sensor which measures pressure through the wall of associated tubing and is available from Data Instruments of Lexington, Mass., Model AB. Analog-to-Digital Converter 14 is available from National Semiconductor, Inc. of Santa Clara, Calif., ADC-0817. ADC 14 can be interfaced to microprocessor 15 using interface circuitry such as the 6821 Interface Adaptor from Motorola, Phoenix, Ariz. Microprocessor 15 is a Motorola 68000. The latter and its supporting peripherals are commercially available from Motorola. Programmable Timing Module 17 may be a Motorola PTM 6840. Driver Amplifier 18 may be a TBM-105 translator available from Superior Electric, Inc., Bristol, Conn. Stepper motor 16 may be a SLO-SYN®, M063 Series also available from Superior Electric. Finally, peristaltic pump 13 may be a Master-Flex® A-7016-20 available from the Cole Palmer Instrument Co., Chicago, Ill.

It should be appreciated that while the concept in carrying out the present invention will always be invoked, different modes of driving the peristaltic pump may be utilized without departing from the spirit of the present invention. Thus, the output of microprocessor 15 may be converted back to an analog signal using a digital-to-analog converter. The analog output may then be applied to a voltage-to-frequency converter the output of which is then applied to driver amplifier 18. Alternatively, the output of the digital-to-analog converter may be utilized to drive a d.c. motor without further conversion.

Having thus described our invention, what we claim as new, and desire to secure by Letters Patent is:

1. A system for setting the speed of a peristaltic pump when the pump input pressure $P_o$ varies from zero said pump having a pressure vs flow rate characteristic which includes a family of curves each of which, for pressures equal to and greater than zero, exhibits a constant or increasing flow rate with increasing pressure and, for pressures less than zero, exhibits a linearly decreasing flow rate with decreasing pressure over at least a portion of said pressures less than zero comprising:

means for sensing said pump input pressure $P_o$ when it varies from zero and providing an analog output representative thereof, means for converting said analog output into digital form, microprocessor means connected to said means for converting for providing an incremental output $P_i/(P_i - P_o)$ when $P_o$ is negative or an incremental output $P_i/(P_i + P_o)$ when $P_o$ is positive in digital form which is representative of the amount by which the speed $S_o$ of said pump is changed to provide another speed S which will maintain a constant flow rate $Q_o$ when said pump input pressure $P_o$ varies from zero said incremental output being determined from the equations $Q/Q_o = P_i/(P_i \pm P_o)$, $Q = KS$ and $Q_o = KS_o$ where $Q$ = equivalent flow rate at zero pressure required to provide constant flow rate $Q_o$ when $P_o$ varies from zero,
   $Q_o$ = constant desired flow rate provided in digitized form as an input to said microprocessor,
   $P_i$ = pressure at which extrapolated linear portions of the curves of the pump characteristic intersect the pressure axis,
   $P_o$ = pump input positive or negative pressure provided in digitized form as an input to said microprocessor,
   $S$ = speed at which pump must be driven to provide $Q_o$ when $P_o$ varies from zero,
   $S_o$ = speed at which pump is driven to provide $Q_o$ when $P_o$ is equal to zero,
   $K$ = pump constant provided in digitized form as an input to said microprocessor and, means responsive to said incremental output connected to said microprocessor means for changing the speed $S_o$ of said pump to said another speed S.

2. A system for setting the speed of a peristaltic pump according to claim 1 wherein said means for sensing pump input pressure and for providing an analog output is a noninvasive pressure sensor.

3. A system for setting the speed of a peristaltic pump according to claim 1 wherein said means for converting is an analog-to-digital converter.

4. A system for setting the speed of a peristaltic pump according to claim 1 wherein said means for changing the speed includes a programmable timer connected to said microprocessor which provides a variable frequency square wave output, and a stepper motor connected to said pump and said programmable timer responsive to said variable frequency output to set the speed of said pump to said another speed.

5. A system for setting the speed of a peristaltic pump when the pump input pressure $P_o$ drops below zero said pump having a pressure vs flow rate characteristic which includes a family of curves each of which, for pressures equal to and greater than zero, exhibits a constant flow rate and, for pressures less than zero, exhibits a linearly decreasing flow rate with decreasing pressure over at least a portion of said pressures less than zero comprising:

means for sensing said pump input pressure $P_o$ when it drops below zero and providing an analog output representative thereof, means for converting said analog output into digital form, microprocessor means connected to said means for converting for providing an incremental output $P_i/(P_i - P_o)$ in digital form which is representative of the amount by which the speed $S_o$ of said pump is changed to provide another speed S which will maintain a constant flow rate $Q_o$ when said pump input pressure $P_o$ is less than zero said incremental output being determined from the equations $Q/Q_o = P_i/(P_i - P_o)$, $Q = KS$ and $Q_o = KS_o$ where $Q$ = equivalent flow rate at zero pressure required to provide constant flow rate $Q_o$ when $P_o < 0$,
   $Q_o$ = constant desired flow rate provided in digitized form as an input to said microprocessor,
   $P_i$ = pressure at which extrapolated linear portions of the curves of the pump characteristic intersect the pressure axis,
   $P_o$ = pump input negative pressure provided in digitized form as an input to said microprocessor,
   $S$ = speed at which pump must be driven to provide $Q_o$ when $P_o$ drops below zero,
   $S_o$ = speed at which pump is driven to provide $Q_o$ when $P_o$ is equal to or greater than zero,
   $K$ = pump constant provided in digitized form as an input to said microprocessor and, means responsive to said incremental output connected to said microprocessor means for changing the speed $S_o$ of said pump to said another speed S.

6. A system for setting the speed of a peristaltic pump according to claim 5 wherein said means for sensing pump input pressure and for providing an analog output is a noninvasive pressure sensor.

7. A system for setting the speed of a peristaltic pump according to claim 5 wherein said means for converting is an analog-to-digital converter.

8. A system for setting the speed of a peristaltic pump according to claim 5 wherein said means for changing the speed includes a programmable timer connected to said microprocessor which provides a variable frequency square wave output, and a stepper motor connected to said pump and said programmable timer responsive to said variable frequency output to set the speed of said pump to said another speed.

9. A system for setting the speed of a peristaltic pump when the pump input pressure $P_o$ goes above zero said pump having a pressure vs flow rate characteristic which includes a family of curves each of which, for pressures greater than zero, exhibits a linearly increasing flow rate with increasing pressure and, for pressures less than zero, exhibits a linearly decreasing flow rate with decreasing pressure over at least a portion of said pressures less than zero comprising:

means for sensing said pump input pressure $P_o$ when it goes above zero and providing an analog output representative thereof, means for converting said analog output into digital form, microprocessor means connected to said means for converting for providing an incremental output $P_i/(P_i+P_o)$ in digital form which is representative of the amount by which the speed $S_o$ of said pump is changed to provide another speed $S$ which will maintain a constant flow rate $Q_o$ when said pump input pressure $P_o$ is greater than zero said incremental output being determined from the equations $Q/Q_o = P_i/(P_i+P_o)$, $Q = KS$ and $Q_o = KS_o$ where $Q$ = equivalent flow rate at zero pressure required to provide constant flow rate $Q_o$ when $P_o < 0$, $Q_o$ = constant desired flow rate provided in digitized form as an input to said microprocessor, $P_i$ = pressure at which extrapolated linear portions of the curves of the pump characteristic intersect the pressure axis, $P_o$ = pump input positive pressure provided in digitized form as an input to said microprocessor, $S$ = speed at which pump must be driven to provide $Q_o$ when $P_o$ goes above zero, $S_o$ = speed at which pump is driven to provide $Q_o$ when $P_o$ is equal to zero, $K$ = pump constant provided in digitized form as an input to said microprocessor and, means responsive to said incremental output connected to said microprocessor means for changing the speed $S_o$ of said pump to said another speed $S$.

* * * * *